US012109437B2

(12) United States Patent
Dipasquale (10) Patent No.: US 12,109,437 B2
(45) Date of Patent: Oct. 8, 2024

(54) MEDICAL DEVICE FOR RADIOTHERAPY AND METHOD OF MANUFACTURING THE SAME

(71) Applicant: HÔPITAUX UNIVERSITAIRES DE GENÈVE, Geneva (CH)

(72) Inventor: Giovanna Dipasquale, Veyrier (CH)

(73) Assignee: HÔPITAUX UNIVERSITAIRES DE GENÈVE, Geneva (CH)

( * ) Notice: Subject to any disclaimer, the term of this patent is extended or adjusted under 35 U.S.C. 154(b) by 754 days.

(21) Appl. No.: 17/292,850

(22) PCT Filed: Nov. 13, 2019

(86) PCT No.: PCT/EP2019/081228
§ 371 (c)(1),
(2) Date: May 11, 2021

(87) PCT Pub. No.: WO2020/099510
PCT Pub. Date: May 22, 2020

(65) Prior Publication Data
US 2021/0393980 A1 Dec. 23, 2021

(30) Foreign Application Priority Data

Nov. 14, 2018 (EP) .................................... 18206344

(51) Int. Cl.
*A61N 5/10* (2006.01)
*B29C 64/386* (2017.01)
(Continued)

(52) U.S. Cl.
CPC ............ *A61N 5/107* (2013.01); *B29C 64/386* (2017.08); *B33Y 50/00* (2014.12); *B33Y 80/00* (2014.12);
(Continued)

(58) Field of Classification Search
CPC ............ A61N 5/107; A61N 2005/1097; A61N 2005/1094; A61N 2005/1096;
(Continued)

(56) References Cited

U.S. PATENT DOCUMENTS 5,014,290 A * 5/1991 Moore ................. A61N 5/1042
378/65
10,016,941 B1 * 7/2018 Beard ................ G05B 19/4097
(Continued)

FOREIGN PATENT DOCUMENTS

| CN | 106667747 A | * 5/2017 | |
| WO | WO-2007085864 A2 | * 8/2007 | ............. A43D 1/025 |
| WO | WO-2009127389 A1 | * 10/2009 | ........... A61N 5/1049 |
| WO | 2015013806 A1 | 2/2015 | |
| WO | WO-2015077881 A1 | * 6/2015 | ............. A61B 6/032 |

*Primary Examiner* — Tarla R Patel
(74) *Attorney, Agent, or Firm* — Thomas Coester Intellectual Property (57) ABSTRACT

The present relates to a positioning and shaping shell manufacturing method for manufacturing a positioning and shaping shell comprising a positioning step consisting in positioning and supporting a target body portion with a transparent body shaper in a predetermined position on a positioning board presenting at least one transparent portion permitting scanning through it, an image acquisition step consisting in a target body portion surface scan imaging also via the transparent portion of the board and said transparent body support, a software computing step where the acquired image data are sent and processed in a processing unit, and a producing step consisting in producing a 3D positioning and shaping shell model via additive or subtractive manufacturing method based in the processed image data.

17 Claims, 4 Drawing Sheets

(51) Int. Cl.
   *B29K 83/00*     (2006.01)
   *B29L 31/00*     (2006.01)
   *B33Y 50/00*     (2015.01)
   *B33Y 80/00*     (2015.01)

(52) U.S. Cl.
   CPC ............... *A61N 2005/1097* (2013.01); *B29K 2083/00* (2013.01); *B29L 2031/753* (2013.01)

(58) Field of Classification Search
   CPC .... A61N 5/1049; B29C 64/386; B33Y 50/00; B33Y 80/00; B29K 2083/00; B29L 2031/753; A61B 90/17; A61B 2090/101
   See application file for complete search history.

(56) References Cited

U.S. PATENT DOCUMENTS

| | | | |
|---|---|---|---|
| 2011/0118527 A1* | 5/2011 | Giesel | B33Y 50/00 600/1 |
| 2014/0206924 A1 | 7/2014 | Nieberding | |
| 2014/0330417 A1* | 11/2014 | Keane | A61B 90/18 700/98 |
| 2016/0185046 A1* | 6/2016 | Littlefield | B29C 64/10 703/1 |
| 2016/0256709 A1 | 9/2016 | Robar et al. | |
| 2017/0361535 A1* | 12/2017 | Ju | A61N 5/1038 |
| 2018/0022018 A1* | 1/2018 | Cambridge | B33Y 50/00 264/308 |
| 2018/0229052 A1* | 8/2018 | Lu | A61N 5/10 |
| 2018/0243112 A1* | 8/2018 | Hand | A61F 2/80 |
| 2018/0317610 A1* | 11/2018 | Golub | B33Y 70/00 |

\* cited by examiner

MEDICAL DEVICE FOR RADIOTHERAPY AND METHOD OF MANUFACTURING THE SAME

TECHNICAL FIELD

The present invention relates to a medical device for radiotherapy and to a method of manufacturing said medical device. More particularly, the invention relates to a medical device improving optimal patient positioning and patient position accuracy for a radiotherapy treatment and to a method of manufacturing said medical device.

BACKGROUND OF THE ART

Nowadays, 3.7 million new patients in Europe are affected by cancer every year, 40% of which are treated with radiotherapy treatment and 30% of which for breast cancer. In summary, one out of three women will develop cancer during their lifetime with the leading cause of death being breast cancer. More than half of these will receive radiotherapy as part of their treatment.

In radiotherapy, high intensity X-rays are used to destroy the tumor while trying to minimize the damage to surrounding healthy tissue. To target precisely the tumor, one uses complicated irradiation patterns. However, this only works if the patient does NOT move during a treatment involving multiple sessions and therefore repositioning from one session to the next must be identical.

More particularly, radiotherapy treatment usually consists of one to about thirty-seven sessions of radiotherapy depending on the treated organ, and usually can be planned as one per day and/or five per week. Each session usually comprises several steps, among which the preparation of the patient, often a Magnetic Resonance Imaging (MRI), generation of Computer Tomography (CT) image in the treatment position, planning and finally the treatment. Of course, from one session to another, the target organ/body location needs to be accurately positioned in the same position to provide a reliable treatment in the session. There is therefore a daily imaging to verify the position of the patient which consists of X-ray or megavoltage planner-images, cone beam CT or MRI-imaging through MR linear accelerators.

Positioning therefore usually lasts for about 20-30 minutes per session which is an enormous waste of time. In addition to this, repositioning of the patient is never 100% accurate which leads to around 10 mm extra margin around the target, a daily X-ray imaging, which increases the risk of new cancers and side effects such as irradiation of the neighboring organs such as the heart and the lung. This positioning requirement is often also uncomfortable or painful for the patient.

In case of breast cancer treatment, one way to better irradiate the affected breast is to have the patient lying face down, also called prone position, on the treatment board. However, patient repositioning is currently very difficult in prone.

Prone positioning is very difficult for women that were operated on for breast cancer due to reduced arm mobility and pain. This reflects in poor patient positioning reproducibility during radiotherapy treatment.

There is therefore a need for a means to address these issues in order to be able to treat patients in the best possible way.

In this regard, a primary objective of the invention is to solve the above-mentioned problems and more particularly to provide a medical device providing optimal patient positioning and improving patient repositioning accuracy for radiotherapy treatment.

It has to be noted that in the present invention, the term radiotherapy of course refers to X-rays, but also to proton, carbon ions, neutrons therapy and flash therapy.

SUMMARY OF THE INVENTION

The above problems are solved by the present invention.

A first aspect of the invention is a patient's body portion positioning and shaping shell manufacturing method for manufacturing a shell comprising a positioning step that consists in positioning and supporting a target body portion of a patient's body with a transparent body shaper in a predetermined position on a positioning board presenting at least one transparent portion permitting scanning through it, an image acquisition step that consists of a target body portion surface scan imaging via the transparent portion of the board and said transparent body support, a software computing step where the acquired image data are sent and processed in a processing unit, and a producing step that consists of producing a 3D positioning and shaping shell model via an additive or subtractive manufacturing method based on the processed image data. The particular advantages of this device of the invention being similar to the ones of the method of the first aspect of the invention, they will not be repeated here. It has to be noted here that although the board can, of course, support the patient in a horizontal position, the board is not limited to it and may support the patient (or part of him) in a different position/orientation, like standing next to an X-ray machine for radiology or seating on a chair or the same.

By the expression additive or subtractive manufacturing method it is meant that it is possible to transfer the shell model created via steps of the computer implemented program to
- create a mold via 3D printing to create the shell by filling the mold (example using silicon);
- thermoforming;
- use of CNC machines;
- create the shell using a pin-matrix system that shapes to the surface form to be created. The pins/rods can present a small point allowing to create holes in a thin sheet, such as and not limited to PETg, HIPS, ABS, Polystyrene, Polyproperlene, Polycarbonate, Polyethylene, Acrylic PMMA, that via thermofolding and vacuum compression will create the shell;
- create the shell using a paired pin-matrix system allowing to compress a dedicated material while one set of pins/rods present a small needle like point allowing to create holes in the plastic because the corresponding parallel Pin/rod will allow receiving the needle.

Preferably, the target body portion is either one of a body portion to be treated and/or a body portion to be spared.

According to a preferred embodiment of the present invention, the additive manufacturing method is 3D printing.

Preferably, the target body portion is the breast.

Advantageously, the surface scan imaging is comprising in the group composed of Magnetic Resonance or Computer Tomography.

Preferably, the transparent portion of the board is made of a transparent acrylic such as Plexiglas® or glass, or other transparent plastics. Thus, imaging is facilitated.

A second aspect of the invention is a patient positioning device for use in a radiotherapy treatment process comprising a positioning board, and a positioning and shaping shell manufactured according to the first aspect of the invention, said shell reproducing a patient's target body portion shape and adapted to be installed on the positioning board so as to receive and immobilize said radiotherapy target body portion of the patient's body. In this manner, the patient can be rapidly and comfortably positioned in a predetermined and recurrent manner at each session.

According to a preferred embodiment of the present invention, the positioning and shaping shell comprises a hollow portion adapted to receive and house a specific bolus. Thus, the treatment is improved.

Advantageously, the positioning and shaping shell is made of silicone and/or thermoplastic materials. In this manner, it can be easily manufactured.

Furthermore, the positioning and shaping can be made of a transparent material allowing the use of optical monitoring systems capable of "seeing" through the transparent materials, such as laser scanners, to detect movements of the patient under the shell shaping the patient body.

According to a preferred embodiment of the present invention, the patient positioning device is adapted to position the patient in a prone position. In this manner, the patient is positioned in the most effective position for breast cancer treatment.

Advantageously, the positioning board comprises a tilting means adapted to tilt and/or move said target body portion of the patient's body. Thus, one can reduce the dose to undesired zones of the body.

Preferably, the patient positioning device further comprises attaching means for attaching the positioning and shaping shell to the positioning board. Thus, the shell is strongly immobilized on the board.

According to a preferred embodiment of the present invention, the positioning and shaping shell is adapted to shape the patient's target body portion. In this manner, the body of the patient can be shaped as needed for a hyperthermia session.

Advantageously, the positioning and shaping shell is made of two complementary detachable elements. In this manner, bolus could be supported/housed even in very complicated shapes of shells.

A third aspect of the invention is a computer implemented program running the method of the second aspect of the invention. The particular advantages of this device of the invention being similar to the ones of the method of the first aspect of the invention, they will not be repeated here.

A fourth aspect of the invention is a transparent body shaper to be used in the positioning shell manufacturing method of the second aspect of the invention adapted to support and position a predetermined target body portion in a specific position adapted for an optimal radiotherapy treatment process.

In addition, the system can comprise other devices next to or in contact with the patient with the shapers having allowed to position them as necessary. These other devices can be, but are not limited to: sensors, monitoring systems, detectors, feeding systems, anesthesia systems, treatment or imaging systems (ex. ultrasound systems), cooling systems, and elements such as metamaterials.

Furthermore, the shell, in addition to its positioning and shaping function, can have further functions such as beam stopping, and/or radiation modulation.

The above aspects of the invention confer, in prone breast treatment, approximately 50% more positioning accuracy, more comfort for patients, less side effects such as lung and heart irradiation, less pre-treatment X-ray imaging, less risk of radio-induced cancer and less time for repositioning from 30 min to 5-10 min.

BRIEF DESCRIPTION OF THE DRAWINGS

Further particular advantages and features of the invention will become more apparent from the following non-limitative description of at least one embodiment of the invention which will refer to the accompanying drawings, wherein.

DETAILED DESCRIPTION OF THE INVENTION

The present detailed description is intended to illustrate the invention in a non-limiting manner since any feature of an embodiment may be combined with any other feature of a different embodiment in an advantageous manner.

In general, a first aspect of the present invention refers to a new positioning and shaping shell manufacturing method including imaging through a transparent portion of a board and produced by additive or subtractive manufacturing using dedicated computer implemented software.

Figure 1:
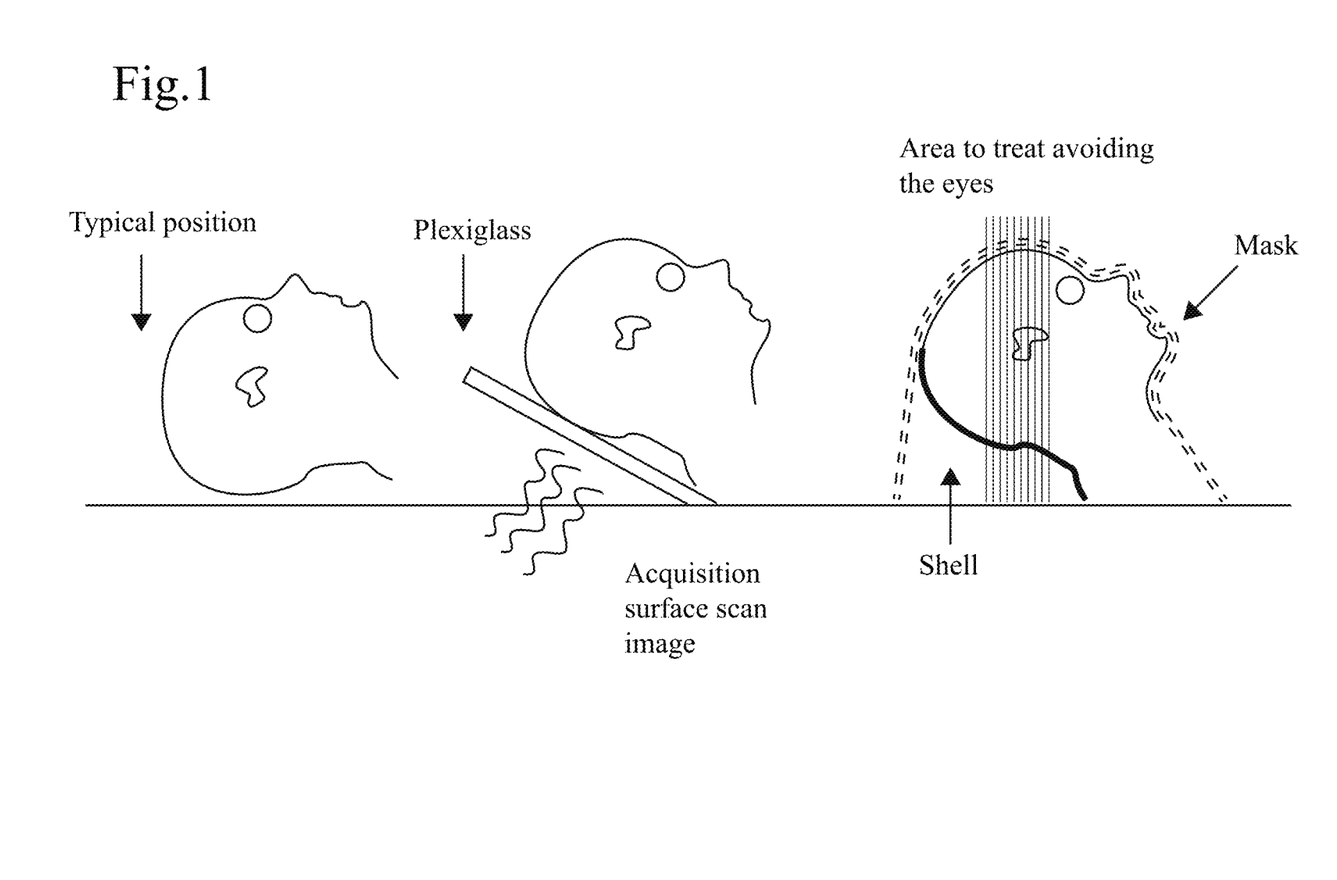
FIG. 1 is a schematic that illustrates the process of creating a positioning and shaping shell using a surface scanner through a transparent element tilting a head of a patient according to an embodiment of the present invention.

More particularly, FIG. 1 represents a first aspect of the invention which is a process of using a surface scanner through a transparent element tilting a head of a patient avoiding radiation to the eyes i.e. positioning optimization and creating a positioning and shaping shell for this purpose as well as for patient positioning accuracy, the positioning and shaping shell is available before CT planning and therefore included in the immobilization mask.

Figure 2:
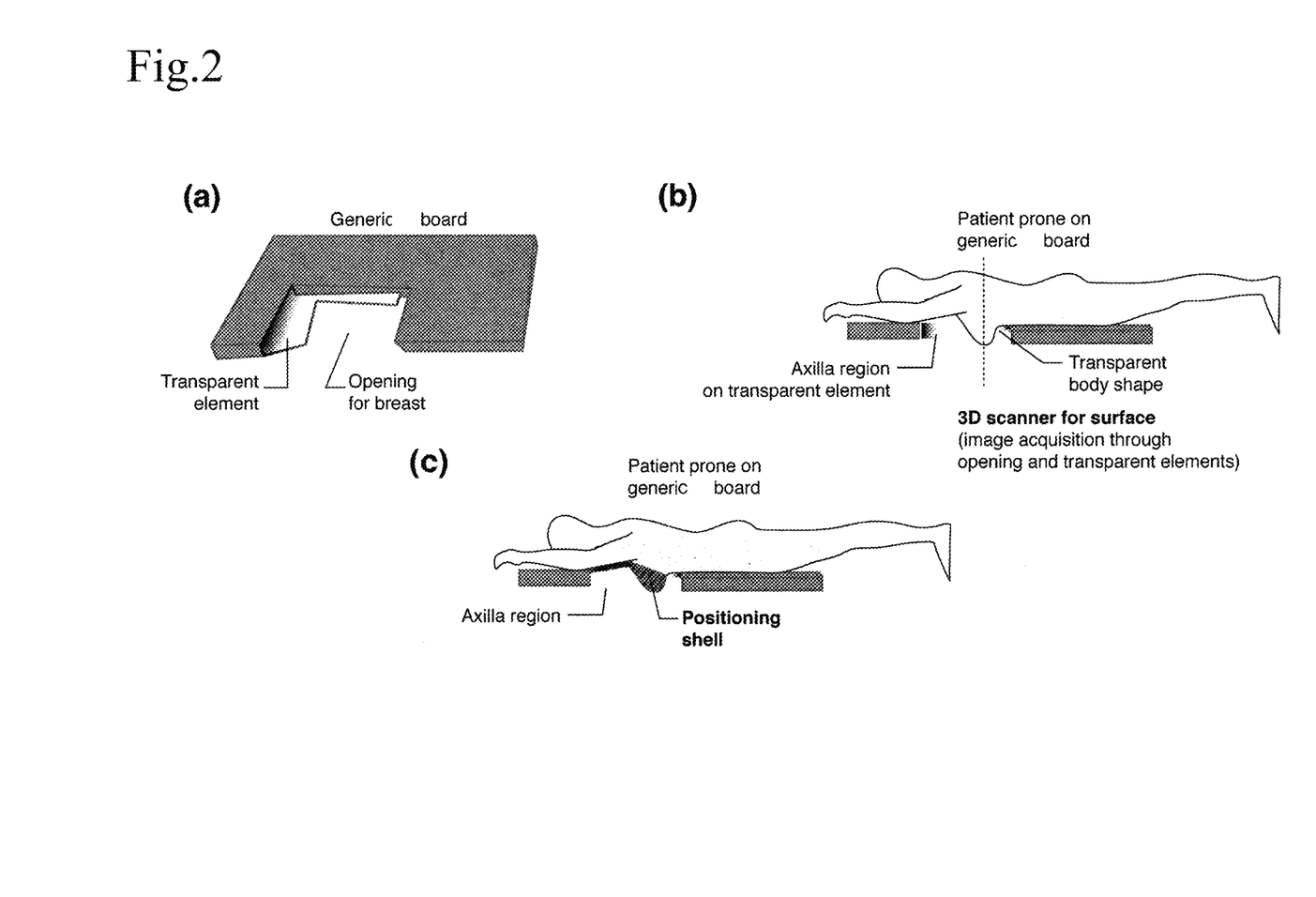
FIG. 2A to 2C shows the process of producing a positioning and shaping shell for prone breast treatment according to the present invention.

On the other hand, FIGS. 2a to 2c show an alternative process of producing a positioning and shaping shell for prone breast treatment according to another aspect of the present invention. FIG. 2a shows an example of a positioning board with transparent elements, FIG. 2b shows the patient on the positioning board for image via surface scanner and FIG. 2c shows the situation once the positioning and shaping shell has been printed, the patient on the board with the positioning and shaping shell.

More particularly, these aspects of the invention are specific embodiments of the procedure for manufacturing a patient's body portion positioning and shaping shell comprising a positioning step consisting in positioning and supporting a target body portion of a patient's body with a transparent body shaper in a predetermined position on a positioning board presenting at least one transparent portion permitting scanning through it. In other words, the body shaper allows positioning the body part to image in the optimal position for his future treatment (for imaging treatment or radiotherapy (RT) boluses insert after planning in RT). Then the process comprises an image acquisition step consisting in a target body portion surface scan imaging via the transparent portion of the board and said transparent body support, a software computing step where the acquired image data are sent and processed in a processing unit, and a producing step consisting in producing a 3D positioning and shaping shell model via additive or subtractive manufacturing method based in the processed image data.

This shell can be used on the patient for CT/MRI image acquisition for radiotherapy RT, bolus insert on the external part of the shell, after CT/MR imaging acquisition for radiotherapy planning is used to determine the bolus characteristics, performing X-ray/MRI/CT image pre- and/or during biopsy, performing X-ray/MRI/CT image for anatomy diagnosis and injection products (for example the injection to replace cartilage), imaging and repeating images to stage the tumor regression progression helping the medical staff to view the body in the same orientation allowing image registration of different imaging modalities example MRI/PET/CT, modifying the body part as needed such as flatten a region for a hyperthermia session which is a long treatment that can last 1-2 hours and allow for image registration of hyperthermia information with planning CT/MRI data and keep the body together and avoid movements when RT treatments allow board movements while the beam is on and reduce patient linear accelerator collisions.

During non-coplanar arc treatments and future treatments with the treatment table moving while irradiating the patient, it will be necessary to assure that no collision is possible between the patient and the treatment machine. Therefore, the space around the table and including the patient will need to be modeled in the planning system to avoid collisions. This safe space once defined can be identified prior to the simulated CT by means of transparent walls (curved or linear) that act like body shapers through which the patient's anatomy can be imaged via surface scanners to create positioning shells. This will allow not only to accurately immobilize the patient but also allow the user to know prior to CT simulation if the patient's body position is optimal for the treatment foreseen and avoid collisions at treatment.

This procedure can be useful in several applications including radiotherapy, hyperthermia, biopsy, injections, repeated imaging to verify changes of the investigated area while keeping the body in the same position. It also allows to position a bolus.

Figure 3:
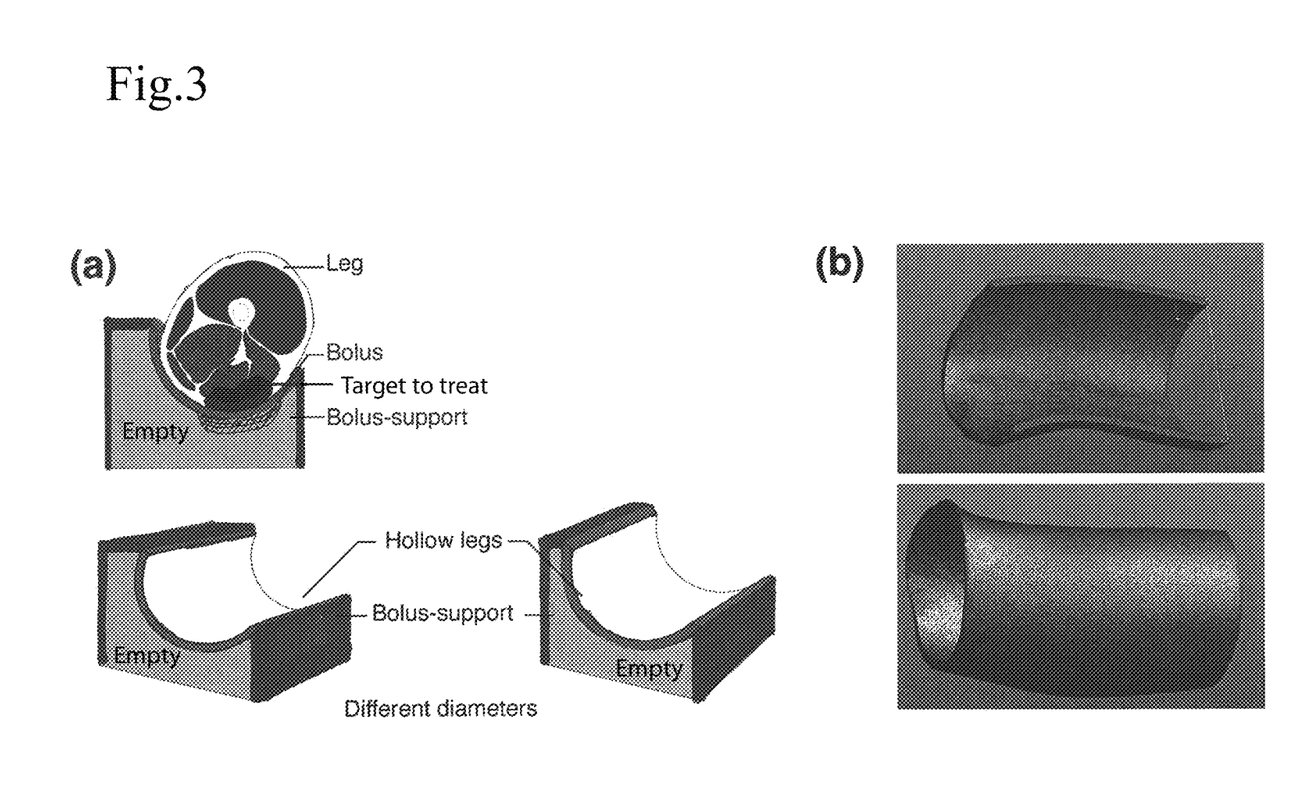
FIGS. 3A and 3B illustrates an example of a positioning and shaping shell created as a leg support of the present invention.

Then, FIG. 3a is described which represents an example of a positioning and shaping shell created as a leg support already available at the CT simulation and in which, from the back it is possible to attach a bolus without the need of a new CT scan. FIG. 3b in its turn shows an example of a leg model acquired from a surface scan image prior CT simulation to customize the shaping shell.

These FIGS. 3a and 3b represent a specific embodiment of a second aspect of the invention which is a positioning device, for use in a radiotherapy treatment process comprising a positioning board, and a silicone or plastic-made positioning and shaping shell reproducing a patient's target body portion shape, preferably comprising a hollow portion adapted to receive and house a specific bolus, and adapted to be installed on the positioning board so as to receive and immobilize said radiotherapy target body portion of the patient's body.

Although the positing board is not represented, it can comprise a titling means adapted to tilt and/or move the target body portion of the patient's body and attaching means for attaching the positioning and shaping shell to the positioning board.

On the other hand, the positioning and shaping shell can be made of two complementary detachable elements. In this manner, bolus could be supported/housed even in very complicated shapes of a shell. This is explained in more detail below in support of FIGS. 4a to 4c.

This allows radiotherapy centers to better cure cancer patients, including breast cancer patients, with less side effects. It leads to more accurate and more time-efficient treatments because of better positioning of the patient.

The device of the present invention allows to better immobilize the target body portion (e.g. the breast or leg or face) using a personalized 3D printed shell. It permits using advanced treatment technique such as protons, and reduces healthy organ irradiation, setup-treatments slot times and imaging radiation.

In case of breast cancer treatment, the shell of the present invention permits increasing the breast opening on the board to also include the supra-clavicular area, an important region to treat in advanced cancers. It also integrates the use of bolus for superficial tumor treatments.

Another aspect of the invention relates to the positioning and shaping shell which is a personalized thin hollow support structure acting as a positioning and shaping bolus-support shell, 3D printed with thermoplastic or other materials, using the patient's surface image acquired with a 3D scanner. This positioning and shaping shell is preferably created larger than the region where the foreseen bolus is required and identified using repairs on the patient's skin to determine its location with respect to the patient's body.

Figure 4A:
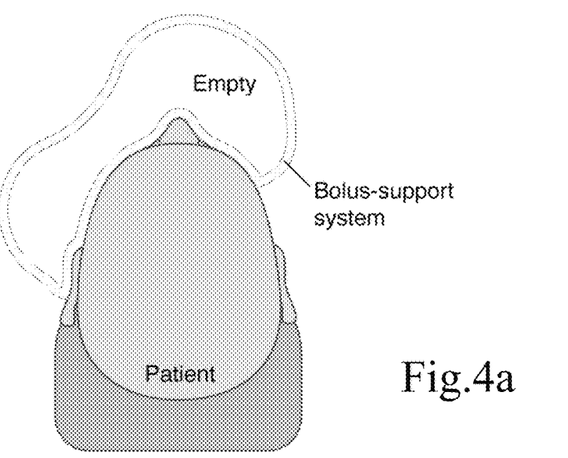
FIG. 4A to 4C represent a positioning and shaping shell according to the present invention.
Figure 4B:
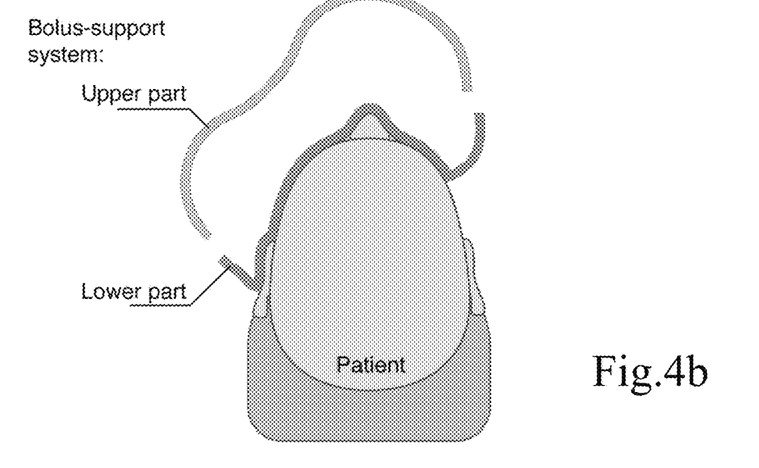
Figure 4C:
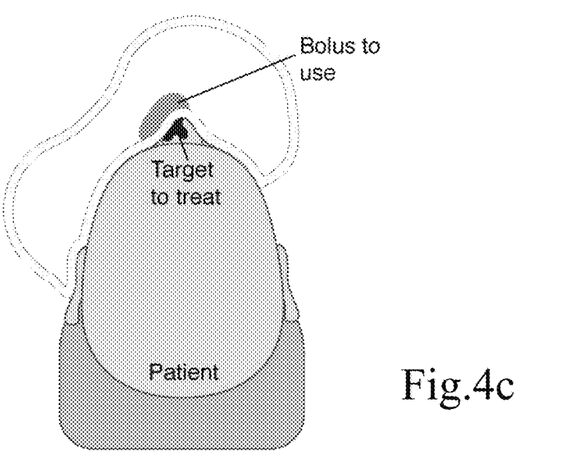

FIGS. 4a to 4c represent a particular embodiment of the positioning and shaping shell which comprises a hollow portion adapted to receive and house a specific bolus, where FIG. 4a shows the bolus shaping shell premade from a surface scan model and ready to be used in combination with immobilizing mask at CT simulation, FIG. 4b shows the two elements that can attach/detach from each other and FIG. 4c shows the presence of the bolus created after CT simulation and planning and hosted in the bolus shaping shell.

The positioning and shaping bolus-support shell preferably has thin physical dimensions and uses material or structures that reduce interactions with radiotherapy treatments fields (photons, electrons, protons or others). This is achieved by using hollow or perforated structures.

Once created the positioning and shaping bolus-support shell is then fitted on the patient prior to any immobilization or positioning and shaping bolus-support shell for CT/MR treatment image acquisition. After radiotherapy simulation and dose planning, the hollow bolus-support structure then hosts the finalized, 3D-printed, optimized bolus by containing or integrating it. In simple cases, a 3D-printed bolus can be placed inside the hollow support structure. In more complicated cases, the upper part of the structure (that can already be attached to an immobilization device) is combined with a lower part of the bolus-support structure. The lower part can be 3D printed using the original's shape, but filled where bolus material is necessary. Very complicated boluses can be created using the flexibility of 3D printers by combining different materials and different filling factors.

Thanks to this bolus-support structure, it is possible to use an optimal bolus for a specific patient and treatment, without compromising on patient's positioning reproducibility or dose distribution. Also, it permits to use 3D-printed boluses without needing to cut thermo-plastic masks to allow for the fitting of the bolus and thus compromising the mask's rigidity and to improve both patient's comfort and immobilization as the bolus is created on measurement from the patient's anatomy creating a perfect fit, even with all accessories necessary to treat the patient (masks, supports, immobilization devices) in place. Finally, it permits avoiding pushing on open skin wounds or painful tissue areas to create the bolus and or fit the accessories. The bolus could even avoid contact with damaged skin if supported on healthy skin or fixed to the mask. The use of a hollow bolus-support structure also allows modification of the space around the patients' body surface without the need of new simulation, masks, supports etc. and a gain in time and department resources.

Alternatively one can use a surface optical system that today is used to monitor the patient during treatments (RT align (Vision RT), Optical Surface Monitoring System (Varian Medical system) to acquire patients' body anatomy to create positioning and shaping bolus-support shell using their repairs to allow for positioning the 3D-printed elements on the patients, also prior to treatment.

One can create for specific areas (such has legs, arms, top of the head etc.) pre-made sets of different sizes of positioning and shaping bolus-support shells that could be adopted for simulation to speed up the treatment planning process and reduce costs. Such systems should allow sterilization or the use of sterile material between the patient's body and the positioning and shaping bolus-support shell for repeated usage.

Further advantages of the positioning and shaping shell are listed below:
- Positions in a reproducible way a body part to treat in the desired position every time;
- Allows support of a bolus in radiotherapy after the bolus position and dimensions are decided following radiotherapy planning (i.e. after CT scan and immobilization tools used);
- Made of MRI compatible material it can be used with CT scan and MRI scans on MRI Linacs to improve image registration and does not interfere with a MRI imaging;
- It can be used for shaping the body to allow Hyperthermia using proper shell material such as silicone that interferes only minimally with the heat transfer;
- It can be used to interface/support imaging systems, such as echography systems, with the patient body to optimize patients position and accuracy while acquiring images/and or other information.

While the embodiments have been described in conjunction with a number of embodiments, it is evident that many alternatives, modifications and variations would be or are apparent to those of ordinary skill in the applicable arts. Accordingly, this disclosure is intended to embrace all such alternatives, modifications, equivalents and variations that are within the scope of this disclosure. For example, the invention is particularly not limited in the different materials which can be used and the radiotherapy treatment devices which can be used in combination with the present invention.

The invention claimed is:

1. Positioning and shaping shell manufacturing method for manufacturing a positioning and shaping shell comprising:
    a positioning step including positioning and supporting a target body portion with a transparent body shaper in a predetermined position on a positioning board, the positioning board presenting at least one transparent portion permitting scanning through it,
    an image acquisition step including partially imaging the target body portion surface via the transparent portion of the positioning board and said transparent body shaper to acquire image data,
    a software computing step where the acquired image data are sent and processed in a processing unit to generate processed image data, and
    a producing step including producing a 3D positioning and shaping shell model via additive or subtractive manufacturing method based in the processed image data.

2. Positioning and shaping shell manufacturing method according to claim 1, characterized in that the additive manufacturing method is chosen from the group of 3D printing, thermoforming, pin-matrix system shaping and the subtractive manufacturing method is chosen from the group of drilling, milling, turning and laser shaping.

3. Positioning and shaping shell manufacturing method according to claim 1, characterized in that the target body portion is a breast.

4. Positioning and shaping shell manufacturing method according to claim 1, characterized in that the image acquisition is performed using a surface scan imaging system selected from the group composed of a surface scanner, Magnetic Resonance Imaging System or Computer Tomography system.

5. Transparent body shaper to be used in the positioning shell manufacturing method of claim 1 adapted to support and position a predetermined target body portion in a specific position adapted for an optimal medical treatment.

6. Patient positioning device for use in a radiotherapy treatment process comprising:
    a positioning board, and
    a positioning and shaping shell manufactured by i) positioning and supporting a target body portion with a transparent body shaper in a predetermined position on a positioning board, the positioning board presenting at least one transparent portion permitting scanning through it, ii) at least partially imaging a target body portion surface via the transparent portion of the positioning board and said transparent body shaper, iii) processing acquired image data in a processing unit to generate processed image data, and iv) producing a 3D positioning and shaping shell model via additive or subtractive manufacturing method based in the processed image data and reproducing a patient's target body portion shape and adapted to be installed on the positioning board so as to receive and immobilize said target body portion.

7. Patient positioning device according to claim 6, characterized in that the positioning and shaping shell comprises a hollow portion adapted to receive and house a specific bolus.

8. Patient positioning device to claim 6, characterized in that the positioning and shaping shell is made of silicone.

9. Patient positioning device according to claim 6, characterized in that the transparent portion of the positioning board is made of a transparent acrylic material.

10. Patient positioning device according to claim 6, characterized in that it is adapted to position the patient in a prone position.

11. Patient positioning device according to claim 6, characterized in that the positioning board comprises a tilting means adapted to tilt and/or move said target body portion.

12. Patient positioning device according to claim 6, characterized in that it further comprises attaching means for attaching the positioning and shaping shell to the positioning board.

13. Patient positioning device according to claim 6, characterized in that the positioning and shaping shell is adapted to shape the patient's target body portion.

14. Patient positioning device according to claim 6, characterized in that the positioning and shaping shell is made of two complementary detachable elements.

15. Patient positioning device according to claim 6, characterized in that it comprise other devices next to or in contact with the patient and with the transparent body shapers to position the patient as necessary, the devices chosen from the group of sensors, monitoring systems, detectors, feeding systems, anesthesia systems, treatment or imaging systems, cooling or heating systems, tracking systems, metamaterials and the same.

16. Patient positioning device according to claim 6, characterized in that it is adapted to at least partially stop a radiotherapy beam and modulate radiation.

17. Patient positioning device according to claim 6, characterized in that its capacity to immobilize said target body portion of a patient's body includes that it prevents patient body movements during treatments so that the patient's body can be translated/rotated during irradiation while avoiding collisions between the patient's body and a treatment machine.

* * * * *